US00PP17518P3

(12) United States Plant Patent
Cowlishaw

(10) Patent No.: US PP17,518 P3
(45) Date of Patent: Mar. 27, 2007

(54) SHRUB ROSE PLANT NAMED 'FRANTASIA'

(50) Latin Name: *Rosa hybrida*
Varietal Denomination: FRAntasia

(75) Inventor: Frank R. Cowlishaw, Derby (GB)

(73) Assignee: Weeks Wholesale Rose Grower, Inc., Upland, CA (US)

( * ) Notice: Subject to any disclaimer, the term of this patent is extended or adjusted under 35 U.S.C. 154(b) by 56 days.

(21) Appl. No.: 10/306,927

(22) Filed: Nov. 29, 2002

(65) Prior Publication Data

US 2004/0107467 P1 Jun. 3, 2004

(51) Int. Cl.
*A01H 5/00* (2006.01)

(52) U.S. Cl. ..... Plt./102
(58) Field of Classification Search ..... Plt./102
See application file for complete search history.

(56) References Cited

PUBLICATIONS

GTITM UPOVROM Citation for 'FRAntasia'as per QZ PBR 001341; Oct. 12, 2000.*
www.HELPMEFIND.com Citation for 'FRAntasia'.*

* cited by examiner

*Primary Examiner*—Kent Bell
(74) *Attorney, Agent, or Firm*—Christie, Parker & Hale, LLP

(57) ABSTRACT

A new variety of Shrub rose suitable for garden decoration, having flowers of purple-blue coloration.

1 Drawing Sheet

Classification: The present invention relates to a new *Rosa hybrida* plant.

Variety denomination: The new plant has the varietal denomination 'FRAntasia'.

BACKGROUND OF THE INVENTION

This invention relates to a new and distinct variety of Shrub Rose. It has as its seed parent the variety known as 'KORizont' (not patented) and an undisseminated seedling of my creation as its pollen parent.

SUMMARY OF THE INVENTION

Among the features which distinguish the new variety from other presently available and commercial rose cultivars known to the inventor are the following combination of characteristics: its unique purple-blue flower coloration, its very upright plant habit, its strong fragrance of clove and spice, its numerous hairs on the rachis and its light green foliage. The plant has a very upright growing habit, suitable for outdoor garden decoration.

Asexual reproduction of the new variety by budding as performed in Kern County and Upland, Calif., shows that the foregoing and other distinguishing characteristics come true to form and are established and transmitted through succeeding asexual propagations. 'FRAntasia' may be asexually propagated by cuttings, budding and grafting.

COMPARISON WITH PARENTS

The new rose may be distinguished from its seed parent, 'KORizont' by the following combination of characteristics: whereas 'FRAntasia' bears semi-double flowers (about 13 to 17 petals) of deep purple-blue coloration, 'KORizont' bears single flowers (about 5 petals) of blended orange pink coloration. The new variety is classified as a shrub with a very upright growth habit, whereas the seed parent is classified as a climber with a significantly more spreading growth habit.

The new variety may be distinguished from its pollen parent, an undisseminated seedling of my creation by the following combination of characteristics: whereas 'FRAntasia' bears very fragrant average size flowers (about 5.9 to about 8.2 cm. in diameter) of deep purple-blue coloration, the undisseminated seedling of my creation bears slightly fragrant significantly smaller flowers of lighter red-purple coloration. The pollen parent is a floribunda rose with a medium compact mature habit, whereas 'FRAntasia' is classified as a shurb rose with a significantly larger more upright growing habit.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (1966) except where common terms of color definition are employed.

DESCRIPTION OF THE NEW VARIETY

The following description is of 3 to 4 year-old rose plants of the new variety grown outdoors in Upland, Calif. in the month of October. Phenotypic expression may vary with environmental, cultural and climatic conditions, as well as differences in conditions of light and soil.

Flower

The new variety sometimes bears its flowers singly, usually in clusters of three or more per stem. Flowers may be borne in irregular moderately pyramidal to somewhat rounded clusters on strong short to long stems (about 35 to about 118 cm.). Outdoors, the plant blooms abundantly and nearly continuously during the growing season. The flowers have a strong clove to spicy fragrance.

Bud

The peduncle is about 1.7 to about 3.2 cm. in length, of average caliper (about 0.2 to about 0.3 cm. in diameter), and usually erect. It is nearly smooth, with few stipitate glands, and numerous hairs. Peduncle color is between 144A and 132C.

Before the calyx breaks, the bud is about 0.8 to about 1.3 cm. in diameter at the widest point, about 1.1 to about 1.6 cm. in length, and very pointed to somewhat ovoid in shape. The surface of the bud bears very few foliaceous appendages and many stipitate glands, usually with slender entire foliaceous parts extending beyond the tip of the bud about ¼ or more of its length. Bud color is between 146B and 132C.

The sepals are about 2.2 to about 2.6 cm. in length and about 0.6 to about 0.9 cm. in width at the widest point. The outer surface color of the sepal is between 146B and 132C. The inner surface color of the sepal is between 138B and 137C and covered with fine wooly tomentum; sepal margins are lined with some stipitate glands and hairs.

As the petals open (after the calyx breaks), the bud is about 1.1 to about 1.5 cm. in diameter at the widest point, about 1.8 to about 2.4 cm. in length, and pointed to moderately ovoid in form. The color of the under surfaces of the newly opened petals is between 71A and 59A. At the point where the petal attaches, there is a somewhat small zone of between 6C and 5C. The color of the upper surfaces of the newly opened petals is between 71A and 79B. At the point where the petal attaches, there is a moderately small zone of between 9C and 11A.

Bloom

When fully open, the bloom ranges from about 5.9 to about 8.2 cm. in diameter. Petalage is semi-double with about 13 to 17 petals and about 2 to 4 petaloids irregularly arranged. When partially open, the bloom form is very cupped to somewhat globular, and the petals are loosely cupped to somewhat spiraled to slightly undulated with petal edges somewhat reflexed outward. When fully open, the bloom form is cupped, and the petals are less cupped to somewhat flat to slightly undulated with petal edges moderately reflexed outward.

Petals

The substance of the petals is moderately heavy and somewhat thin to medium in thickness, with upper surfaces slightly velvety to somewhat satiny and under surfaces more matte to slightly shiny. The outer petals are somewhat round to moderately obovate in shape with rounded apices. The inner petals are broadly obovate in shape with rounded apices and sometimes slightly notched with one or two notches. The petals are about 3.0 to about 3.7 cm. in length and about 2.5 to about 4.2 cm. in width at the widest point. Petal margins are mostly entire.

Newly Opened Flower

The under surface color of the outer, intermediate and inner petals is between 71A and 70B. At the point where the petal attaches, there is a moderately small zone of between 5D and 10D. The upper surface color of the outer, intermediate and inner petals is between 79C and 71B. At the point where the petal attaches, there is a moderately small zone of near 9C.

The general tonality of the newly opened flower is between 79C and 71B.

Three-Day-Old Flower

The under surface color of the outer and inner petals is between 82C and 78C sometimes washed with between 71C and 74C toward the petal edge. At the point where the petal attaches, there is a moderately small zone of between 155D and 69D. The upper surface color of the outer petals is between 79C and 78C sometimes washed with between 75B and 73D. At the point where the petal attaches, there is a moderately large zone of between 76D and 69D.

The general tonality of the three-day-old flower is between 79C and 78C sometimes washed with between 75B and 73D.

On the spent bloom, the petals usually drop off cleanly.

In October in Upland, Calif., blooms on the bush growing outdoors generally last about four to five or more days. Cut roses from plants grown outdoors and kept at normal indoor living temperatures generally last about four to five or more days.

Male Reproductive Organs

Stamens are average in number (average about 80) and are arranged regularly about the pistils; a few are mixed with petaloids. The filaments are of to medium to somewhat long length (about 0.4 to about 0.9 cm.), most with anthers. Filaments are between 7B and 9B in color. The anthers are medium for the class and all open approximately at the same time. Anther color is between 20A and 10C when immature and between 200A and 165B at maturity. Pollen is abundant.

Female Reproductive Organs

Pistils vary in number (average about 30). The styles are moderately even, average to somewhat long in length (about 0.3 to about 0.6 cm.), average in caliper, and loosely bunched to separated. Stigma color is near 11B. Style color is between 2D and 4D sometimes very lightly suffused with near 53D. Ovaries are usually all enclosed in the calyx.

Hips have not been observed on this variety when grown in Upland, Calif.

Foliage

The compound leaves are usually comprised of three to seven leaflets and are borne abundantly. The seven-leaflet leaves are about 9.1 to about 11.8 cm. in length and about 6.6 to about 9.1 cm. in width at the widest point, moderately heavy to somewhat leathery in texture, and somewhat semi-glossy to mostly matte and somewhat rugose in finish. The terminal leaflets are about 4.0 to about 6.7 cm. in length and about 2.3 to about 3.8 cm. in width at the widest point, shaped very oval to somewhat oblong with moderately acute apices and rounded bases. Their margins are usually simply serrate.

The upper surface color of the mature leaf is between 137B and 135B. The under surface color of the mature leaf is between 146B and 135C. The upper surface color of the young leaf is between 146A and 143A, sometimes lightly suffused toward the very edge with between 187B and 183B. The under surface color of the young leaf is between 146B and 135C, sometimes lightly suffused toward the very edge with between 187B and 183B.

The rachis is moderately heavy in caliper and very smooth. The upper side is shallowly grooved with numerous hairs and very few stipitate glands on the edges of the grooves. The under side of the rachis is very smooth with numerous hairs. The rachis color is between 144B and 132C.

The stipules are about 0.9 to about 1.4 cm. in length and moderately wide (about 0.4 to about 0.6 cm.) with medium length straight points that usually turn out at an angle of more than 45 degrees and sometimes recurve toward the stem. The stipules color is between 144B and 132C sometimes heavily suffuses on the young leaves with between 187B and 183B.

The petiole is about 0.3 to about 0.9 cm. in length and about 0.1 to about 0.2 cm in diameter at the widest point. The petiole color is between 144B and 132C.

The plant displays an above average degree of resistance to powdery mildew and rust as compared to other commercial varieties grown under comparable conditions in Upland, Calif. The plant's winter hardiness is between 5*b* and 6*a* on the USDA Plant Hardiness Zone map. The resistance to drought/heat tolerance has been found to be very poor.

Growth

The plant has a very upright tall growing habit (about 175 to about 210 cm. in height and about 0.7 to about 0.88 cm. spread at the widest point), with moderately full branching. It displays very vigorous growth and the canes are somewhat light to medium in caliper for the class.

The color of the major stems is between 148B and 146B. They bear some large prickles that are about 0.5 to about 0.8 cm. in length. The large prickles are moderately hooked downward with a very long broad oval base; prickle color is between 166D and 165C. The major stem bears no small prickles.

The color of the branches is between 144B and 135C. They bear few large prickles that are about 0.4 to about 0.6 cm. in length and of similar shape to the prickles on the major stem. Prickle color is between 162B and 161B sometimes lightly suffused with between 184C and 183D. The branches bear no small prickles.

The color of the new shoots is between 144A and 135C sometimes heavily suffused with between 187B and 183B. They bear some large prickles which are of similar size and shape to the large prickles on the branches; prickle color is near 160A sometimes heavily suffused with between 187C and 183C. The shoots bear few small prickles of similar shape and coloration.

I claim:

1. A new and distinct Shrub rose plant of the variety substantially as described and illustrated herein.

* * * * *

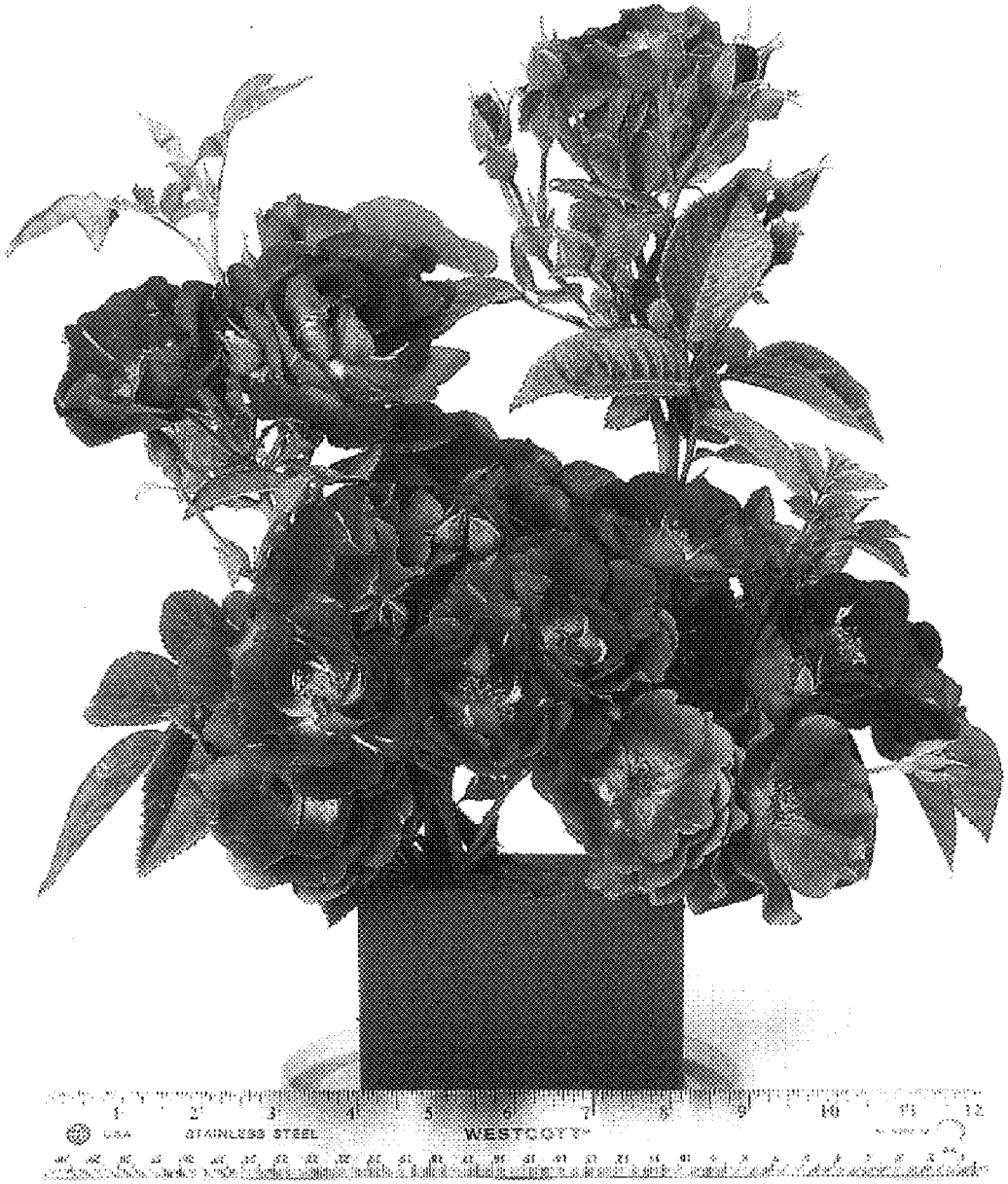
STAINLESS STEEL
WESTCOTT